United States Patent
Halweg-Edwards et al.

(10) Patent No.: US 11,566,241 B2
(45) Date of Patent: Jan. 31, 2023

(54) METHODS AND SYSTEMS FOR MODELING OF DESIGN REPRESENTATION IN A LIBRARY OF EDITING CASSETTES

(71) Applicant: Inscripta, Inc., Boulder, CO (US)

(72) Inventors: Andrea Halweg-Edwards, Boulder, CO (US); Thomas Hraha, Boulder, CO (US); Krishna Yerramsetty, Boulder, CO (US); Shea Lambert, Boulder, CO (US); Miles Gander, Boulder, CO (US); Matthew David Estes, Livermore, CA (US); Chad Douglas Sanada, San Jose, CA (US); Isaac David Wagner, Longmont, CO (US); Paul Hardenbol, Pleasanton, CA (US)

(73) Assignee: Inscripta, Inc., Boulder, CO (US)

( * ) Notice: Subject to any disclaimer, the term of this patent is extended or adjusted under 35 U.S.C. 154(b) by 0 days.

(21) Appl. No.: 17/492,435

(22) Filed: Oct. 1, 2021

(65) Prior Publication Data

US 2022/0106589 A1    Apr. 7, 2022

Related U.S. Application Data

(60) Provisional application No. 63/086,959, filed on Oct. 2, 2020.

(51) Int. Cl.
| | |
|---|---|
| *C12N 15/10* | (2006.01) |
| *G16B 35/20* | (2019.01) |
| *G16B 40/20* | (2019.01) |
| *G16B 35/10* | (2019.01) |

(52) U.S. Cl.
CPC ......... *C12N 15/1089* (2013.01); *G16B 35/10* (2019.02); *G16B 35/20* (2019.02); *G16B 40/20* (2019.02)

(58) Field of Classification Search
None
See application file for complete search history.

(56) References Cited

U.S. PATENT DOCUMENTS

| | | | |
|---|---|---|---|
| 10,287,575 B2* | 5/2019 | Gill | C12N 15/1079 |
| 10,655,114 B1 | 5/2020 | Mijts et al. | |
| 10,665,114 B2* | 5/2020 | Irrgang | G08G 5/0056 |
| 10,731,180 B2* | 8/2020 | Garst | C40B 40/08 |
| 2020/0056192 A1* | 2/2020 | Spindler | C12N 15/90 |

OTHER PUBLICATIONS

Lilleberg et al. 2015 IEEE 14th International Conference on Cognitive Informatics & Cognitive Computing (ICCI*CC), 2015, pp. 136-140.*
Kimothi et al. arXiv: 1608.05949, 2016, p. 1-7.*
PCT/US2021/053235, International Search Report and Written Opinion dated Jan. 7, 2022, 8 pages.

* cited by examiner

*Primary Examiner* — Michael L Borin
(74) *Attorney, Agent, or Firm* — Arnold & Porter Kaye Scholer LLP

(57) ABSTRACT

Disclosed systems and methods relate to predicting the relative representation of genomic variants in an edited cell population, based on the editing cassette design representation in an editing cassette design library used to generate the edited cell population. A library of editing cassette designs is generated, and a feature vector, or sequence embedding, is developed for each design using natural language processing techniques. The feature vector may be based upon sequence attributes and editing kinetics of each cassette design as well as attributes that describe the library context. Features may include sequence embeddings generated from a neural network, linguistic-type distances, and statistical distance summaries thereof. The feature vectors are classified using one or more machine learning models, and the classified feature vectors are used to predict the representation of each design an edited cell population.

20 Claims, 14 Drawing Sheets

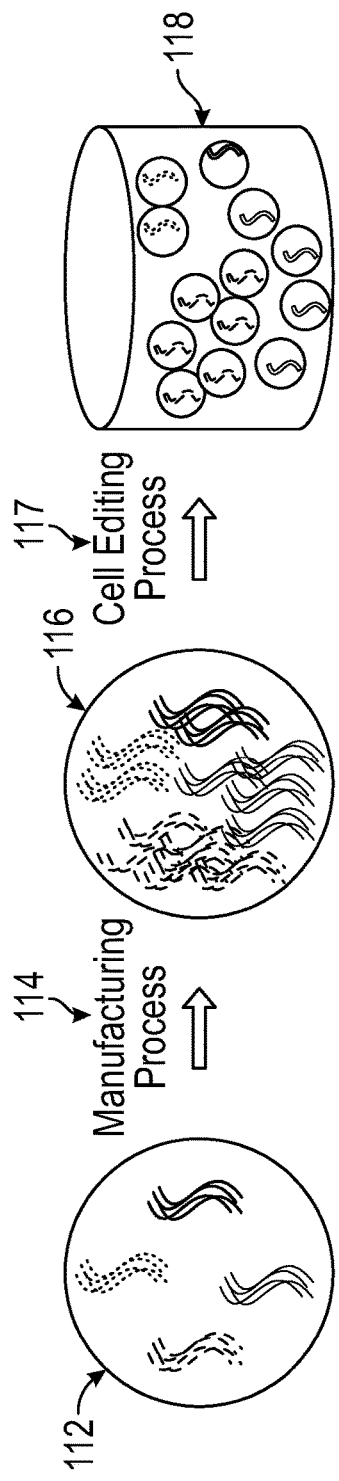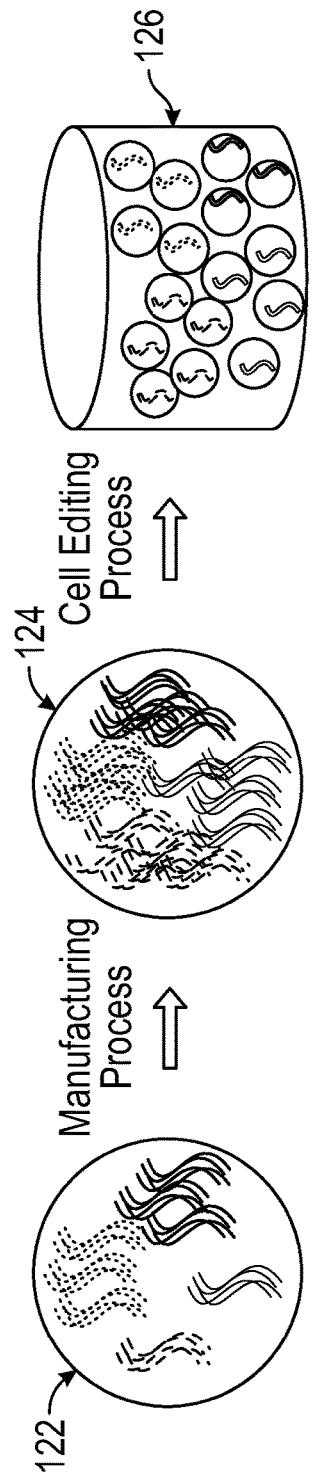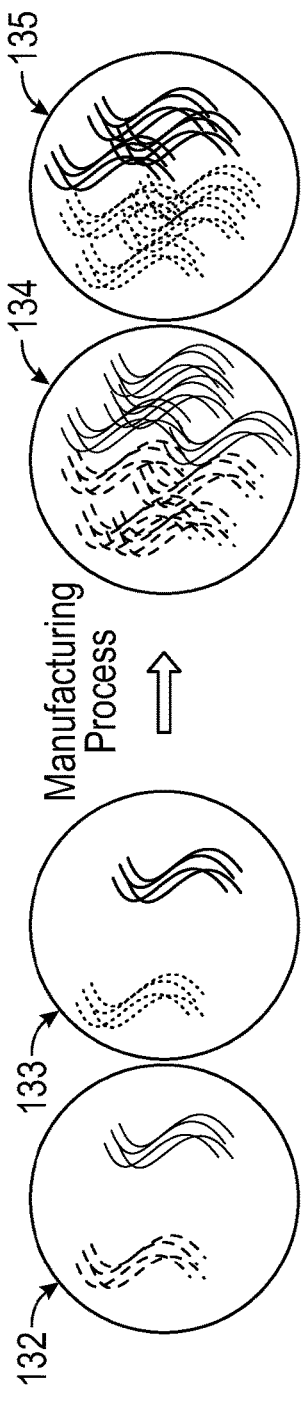

METHODS AND SYSTEMS FOR MODELING OF DESIGN REPRESENTATION IN A LIBRARY OF EDITING CASSETTES

CROSS-REFERENCE TO RELATED APPLICATIONS

This application claims benefit of U.S. provisional patent application Ser. No. 63/086,959, filed Oct. 2, 2021, which is herein incorporated by reference.

BACKGROUND

Field

Embodiments of the present disclosure generally relate to modeling design representations in an editing cassette design library, and more specifically, to predictive modeling of design representation and modification of an editing cassette design library.

Description of the Related Art

A customer ordering a library of editing cassettes to create genetically-edited cells starts with providing sequence editing specifications that include the targeted cell type (e.g., eukaryote, archaea, bacteria, and viral), species, and desired edits (e.g., mutations) that the customer wishes to make in the targeted genome. Edit specifications are used to design one or more libraries of editing cassette designs that are then synthesized. In this context, an editing cassette design is a data representation of an editing cassette that, once synthesized to an editing cassette by an editing cassette manufacturing system, may be deployed to modify a genome of a cell. The libraries of editing cassettes are then used to transform a clonal cell population into a population of genetically modified variants. Using editing cassette design technologies, the cassette design library may contain hundreds, thousands, and tens of thousands (or more) of editing cassette designs in a single library. Using large editing cassette libraries to edit a population of cells allows one to take advantage of efficiencies of scale to create diverse edited cell populations in a single round of editing.

In creating libraries containing many editing cassette designs, and in generating libraries of edited cells, it is can be important that each design in the editing cassette library be represented at approximately the same frequency. If the editing cassette library is biased toward one or more designs, the resulting edited cell population will likely be biased as well. Similarly, if some editing cassettes are likely to edit cells more quickly than others in the same library, then the resulting edit cell population could be biased.

What is needed are methods and systems to predict possible design bias in the editing cassette design library and/or the edited cell population, and use these predictions to modify the composition of the editing cassette library to achieve uniform design representation.

SUMMARY

The present disclosure generally relates to predicting possible design bias in an editing cassette design library and using these predictions to modify the composition of the editing cassette design library to achieve uniform design representation in an edited cell population. A library of editing cassette designs is generated, where a set of features is developed for each editing cassette as well as features of the design library itself. Cassette-centric features include molecular properties like GC content, kmer counts, and folding stability, and feature vectors (e.g., NLP sequence embeddings) derived from cassette design data using natural language processing (NLP) techniques, as well as features that correlate with editing kinetics, including and not limited to the distance between the nuclease cut site and the edit positions, the likelihood that a gRNA is correctly classified as a fast cutter, and the length of sequence upstream and downstream of the edit site on the repair template that is identical to the reference sequence. Features of the cassette design library itself include linguistic-type distances, and statistical distance summaries thereof. Both cassette-centric and library-level features encoded into feature vectors can be used to predict the representation of each design in a manufactured cell population using machine learning techniques.

In one embodiment, a method is disclosed for modifying an editing cassette design library composition that includes receiving an editing cassette design library comprising a plurality of editing cassette designs, each of the plurality of editing cassette designs configured to modify a target sequence to produce a modified sequence, when provided to an automated cell editing system, generating a predictive representation of each modified sequence of each of the plurality of editing cassette designs, and receiving a target representation of each modified target sequence. The method further includes modifying the editing cassette design library to change a number of one of the cassette designs of the design library, generating a second predictive representation of each modified sequence of the modified editing cassette design library such that the second predictive representation is substantially similar to the target representation, and providing the modified editing cassette design library to an editing cassette library manufacturing system, to synthesize one or more manufactured editing cassettes.

Other embodiments provide processing systems configured to perform the aforementioned methods as well as those described herein; non-transitory, computer-readable media comprising instructions that, when executed by one or more processors of a processing system, cause the processing system to perform the aforementioned methods as well as those described herein; a computer program product embodied on a computer readable storage medium comprising code for performing the aforementioned methods as well as those further described herein; and a processing system comprising means for performing the aforementioned methods as well as those further described herein.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

FIG. 1A-C depicts multiple embodiments of modifying a cassette library composition to adjust for changes in editing cassette concentration, according to disclosed embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 2:
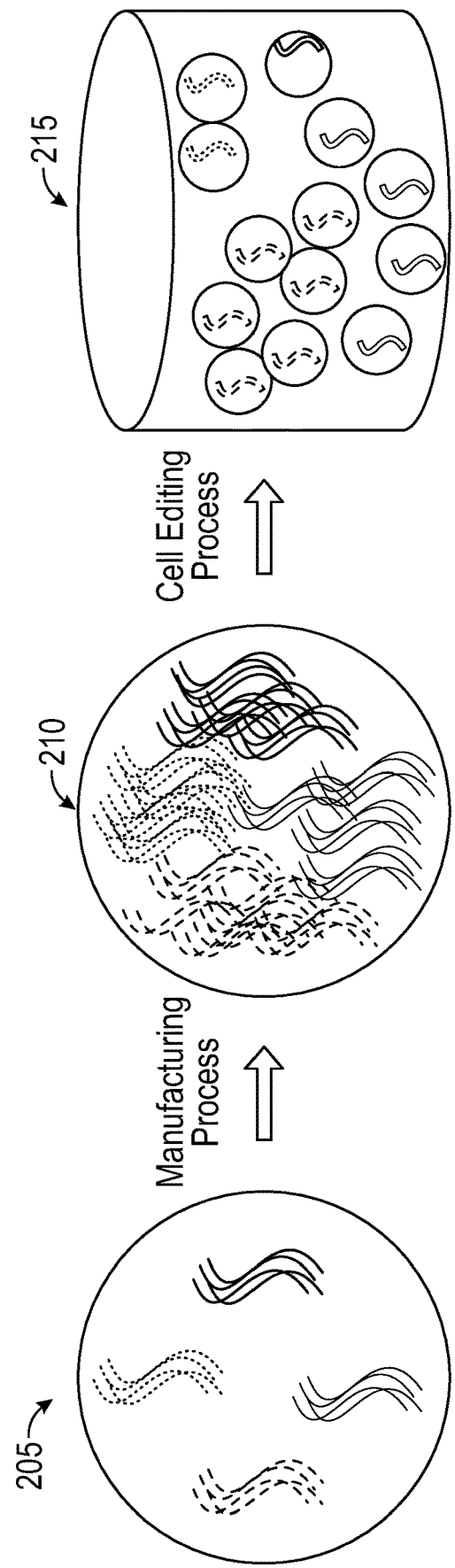
FIG. 2 depicts an embodiment of modifying a cassette library composition to adjust for changes in edited cell population concentration, according to disclosed embodiments.

In the following, reference is made to embodiments of the disclosure. However, it should be understood that the disclosure is not limited to specifically described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the following aspects, features, embodiments, and advantages are merely illustrative and are not considered elements or limitations of the appended claims except where explicitly recited in a claim(s). Likewise, a reference to "the disclosure" shall not be construed as a generalization of any inventive subject matter disclosed herein and shall not be considered an element or limitation of the appended claims except where explicitly recited in a claim(s).

The present disclosure generally relates to predicting possible design bias in an editing cassette library or an edited cell population based on the library, and using these predictions to modify the composition of designs in the editing cassette library to achieve uniform design representation (e.g., low variance) in the library and edited cell population. The library of editing cassettes is generated, where a set of features (e.g., attributes) is developed for each editing cassette design sequence and the library itself. The cassette sequences are provided to an NLP model that is used to train a neural network, generating a set of sequence embeddings representing cassette designs and the library. Linguistic-type distances, and statistical distance summaries thereof, are input to trained models that predict the representation of each design in the edited cell population.

FIGS. 1A-C depict multiple embodiments of modifying an editing cassette design library composition, according to disclosed embodiments.

FIG. 1A depicts a first library 112 of editing cassette designs provided in approximately equal concentration to a manufacturing process 114. During the manufacturing process 114, the editing cassette designs of the first library 112 are amplified to produce DNA oligomer material for use in a cell editing process 117. As is understood by one of skill in the art, the manufacturing process involves amplifying the editing cassette designs to a DNA library before assembling reagent kits that contain all material necessary to build an edited cell population. Following the manufacturing process, an amplified DNA library 116 may contain an unequal concentration of editing cassettes containing individual target sequence designs, that may bias the result within a first edited cell population 118 synthesized from the editing cassettes. The unequal concentrations of editing cassettes in the amplified DNA library 116 are a result of a variety of factors, including, and not limited to, GC bias, the kmer content, sequence length, and sequence similarity (e.g., based on Levenshtein or Hamming distance) of sequences within the editing cassettes of the amplified DNA library 116. Because the manufacturing process can involve amplification and DNA sequence error correction through enzymatic treatment and temperature-induced sequence denaturation and annealing, the nucleotide composition impacts sequence amplification efficiency. One skilled in the art of molecular biology will understand why factors like GC content and sequence similarity impact representation bias in the manufactured DNA library.

FIG. 1B depicts a second library 122 of editing cassette designs, modified according to disclosed embodiments. The second editing cassette design library 122 has been predictively modified according to methods and systems disclosed herein to replicate prior to manufacturing, certain editing cassette designs that are predicted have a lower concentration during the manufacture of an amplified DNA library, with a goal of achieving similar concentrations of editing cassettes in amplified DNA library 124, mitigating the biased result of the amplified DNA library 116. After the cell editing process, the bias seen in the first edited cell population 118 has been mitigated in the second edited cell population 126. The approach depicted in 120 is an "editing cassette replication" strategy.

FIG. 1C depicts a third editing cassette design library 132 and a fourth editing cassette design library 133 of editing cassette designs, a result of the first library 112 having been split into different libraries, which may be carried out as an alternative, or in addition to, the editing cassette replication strategy described above in FIG. 1B. As a result, a third amplified DNA library 134 and a fourth amplified DNA library 135 are produced from the manufacturing process, each containing similar concentrations of amplified DNA populations. By splitting the editing cassette design libraries prior to manufacturing, as opposed to manufacturing all of the editing cassette designs in a single pool, the unequal concentrations of the amplified DNA library 116 may be mitigated. A third and fourth edited cell population (not shown) will similarly have reduced bias as compared to the first edited cell population 118. The editing cassette splitting approach depicted in 130 is a "library splitting strategy."

Figure 3:
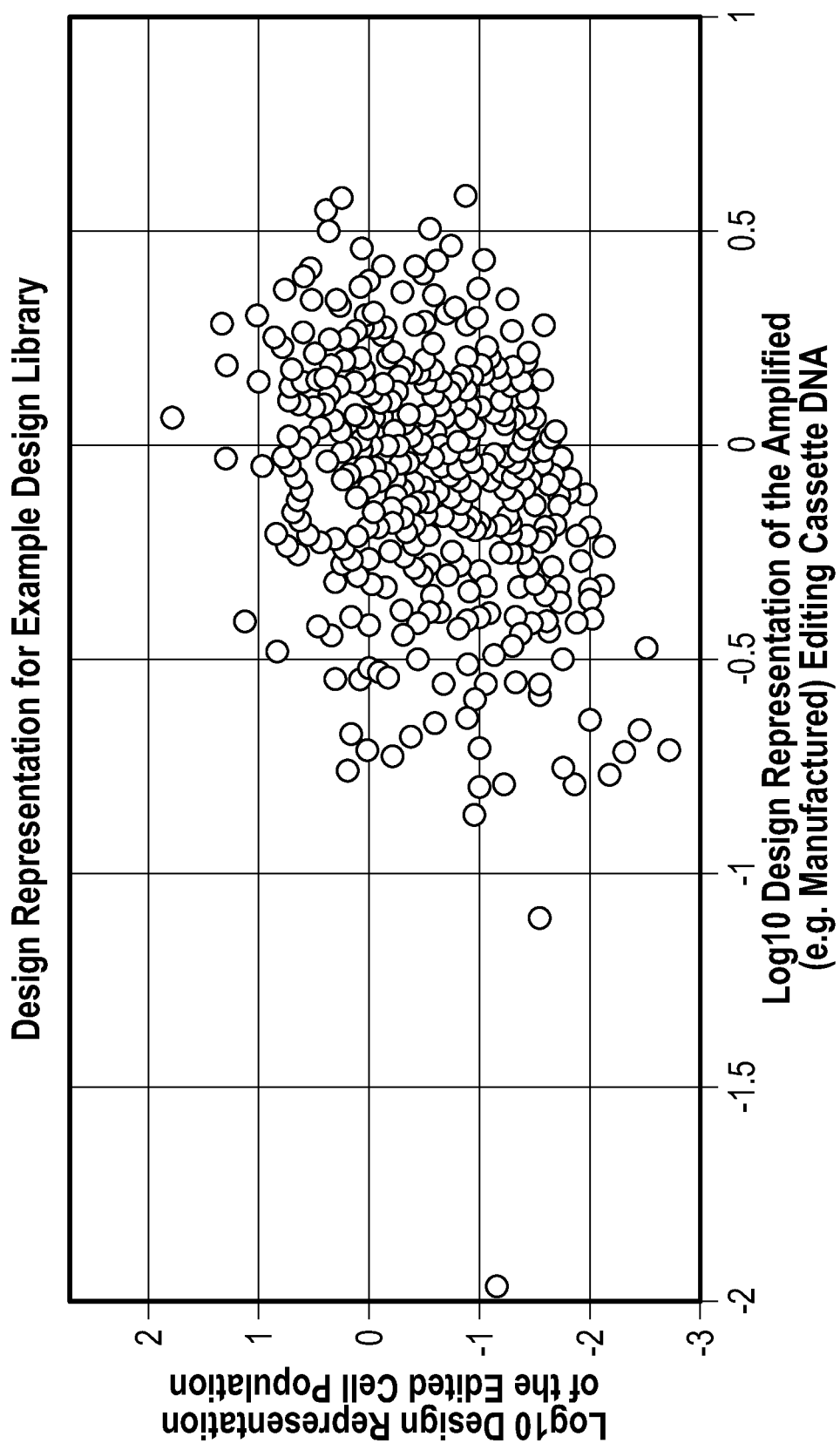
FIG. 3 depicts data demonstrating library cassette design representation, according to some embodiments.
Figure 4:
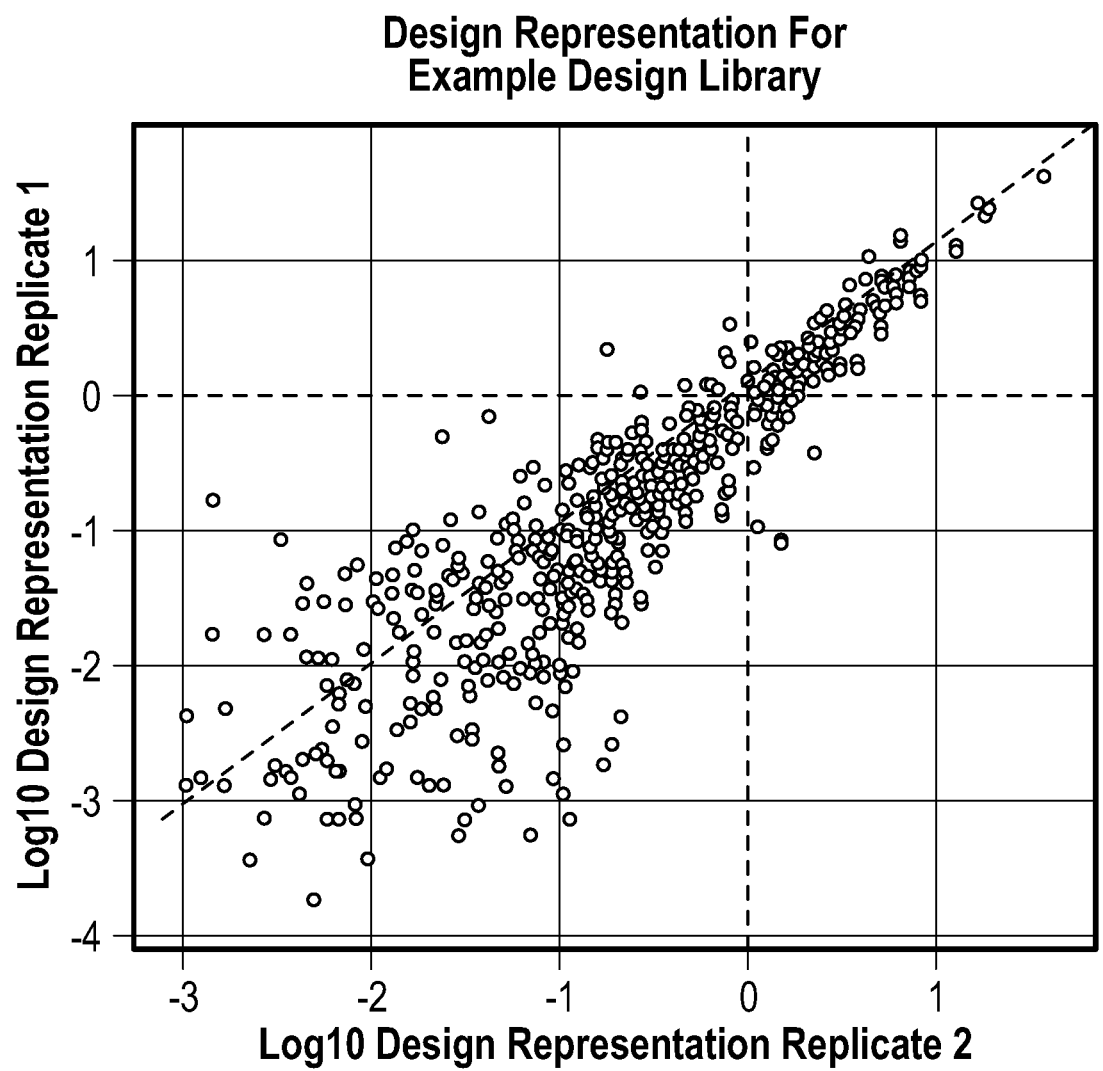
FIG. 4 depicts data demonstrating library cassette design representation, according to some embodiments.
Figure 5:
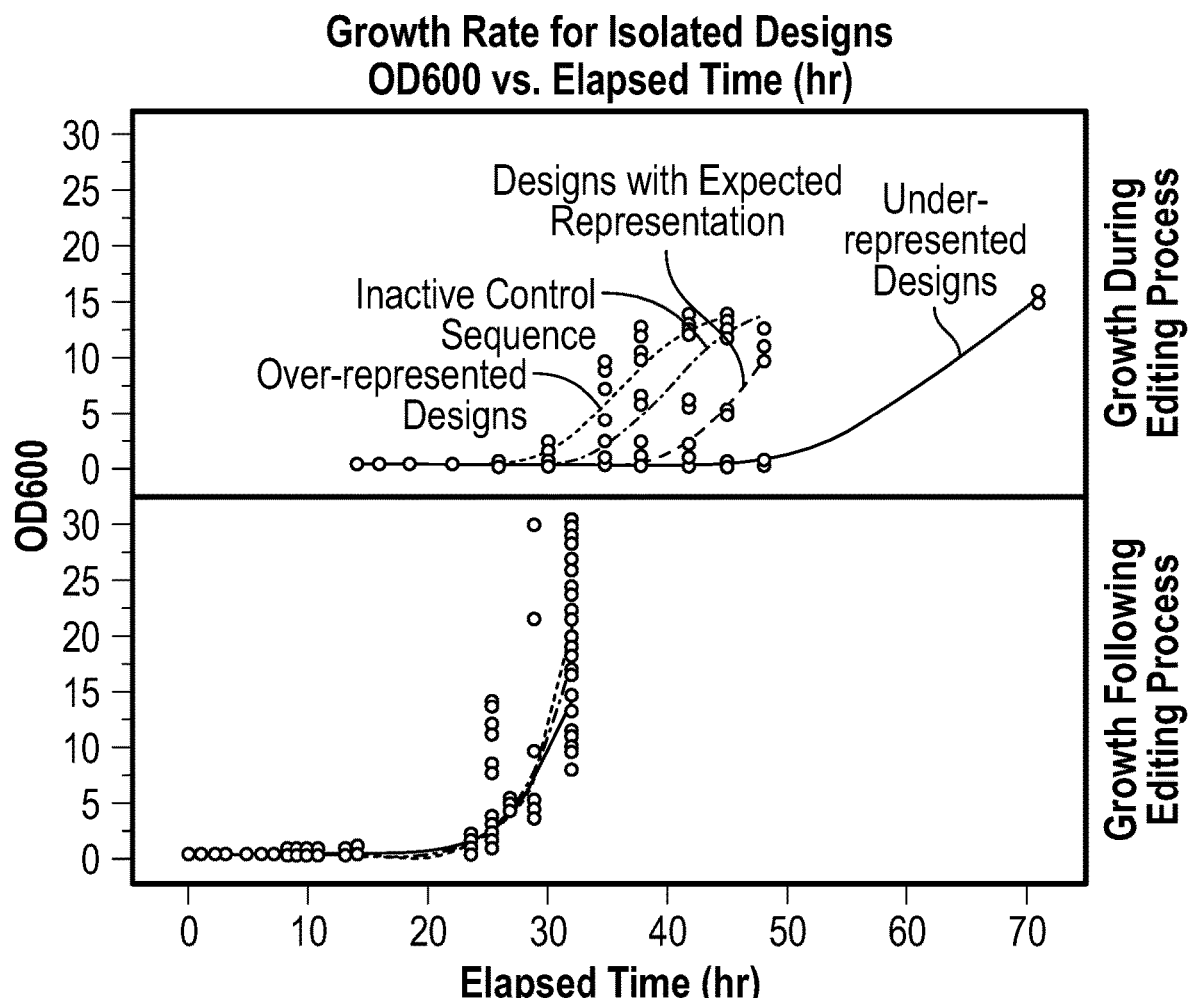
FIG. 5 depicts data demonstrating growth rate for isolated designs, according to some embodiments.
Figure 6:
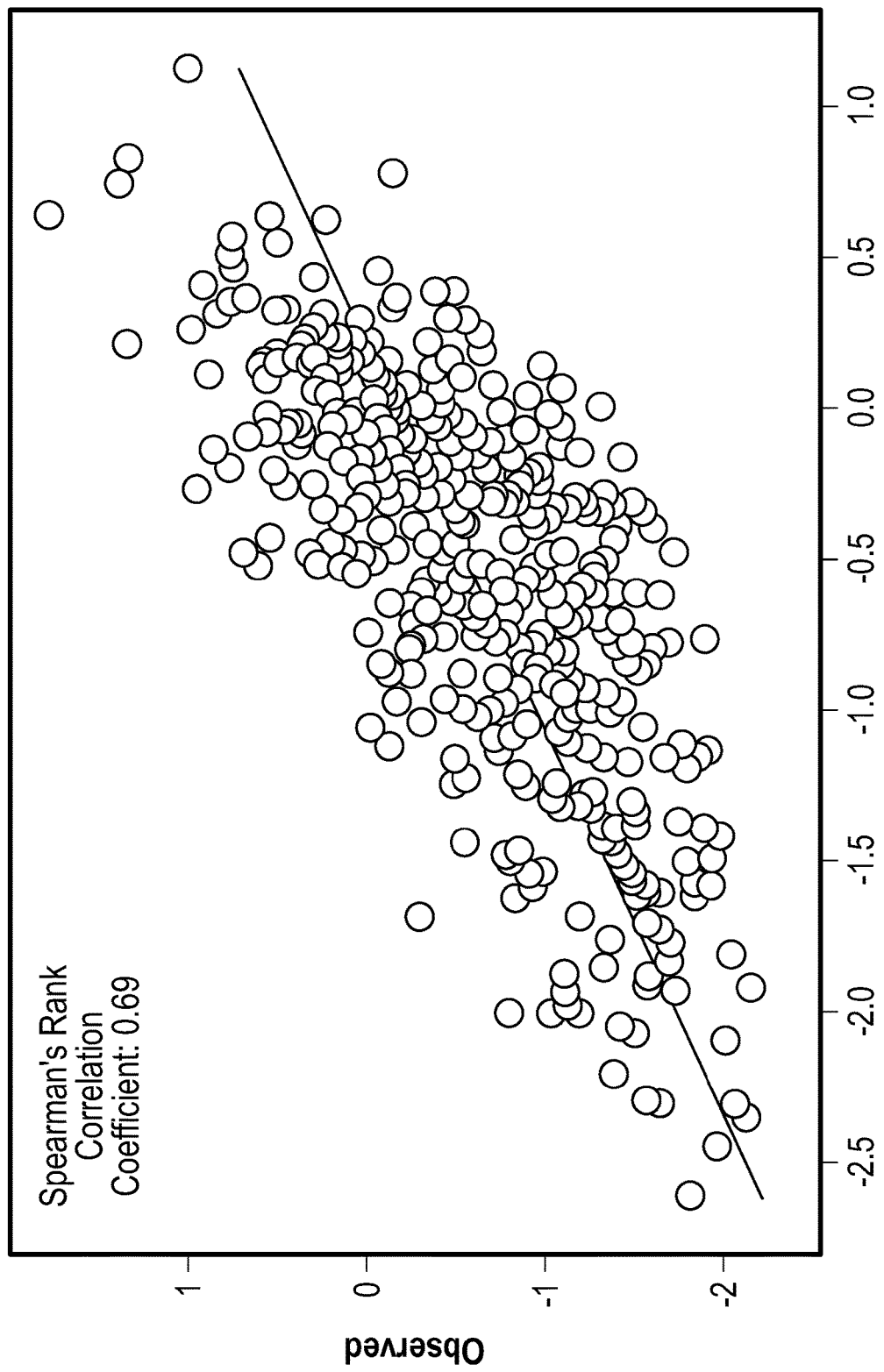
FIG. 6 depicts data demonstrating example model performance according to disclosed embodiments.

FIG. 2 depicts another scenario in which an editing cassette design library 205 is manufactured to amplified DNA library 210, comprising editing cassettes that are in roughly equal concentrations using systems and methods disclosed herein. Following the editing process, the resulting an edited cell population 215 may be comprised of approximately unequal counts of the desired designs. Example data, demonstrating the change in relative design representation when that occurs during the editing process is shown in FIG. 3. This behavior is highly reproducible as demonstrated in FIG. 4 that shows the correlation between two independent cell editing events in which the edited cell population was built from the same sample of the amplified DNA library. The unequal amounts of each type of edited cell are the result of differential kinetic properties inherent to the cassette design, like gRNA folding dynamics and repair template annealing affinity, which result in some cells becoming edited more quickly than others. FIG. 5, top panel, shows cell growth kinetics of clonal cell populations that were transformed with different isolated editing cassettes (e.g. the amplified DNA library is comprised of many copies of a single design sequence), demonstrating that cell growth kinetics during the editing process are dependent upon properties of the editing cassette sequences. Attributes of cassettes that correlate with editing kinetics, include and are not limited to: the length of the edit sequence, the distance between the nuclease cut site and the edit positions, the likelihood that a gRNA is correctly classified as a fast cutter, and the length of repair template sequence upstream and downstream of the edit window that is identical to the reference sequence. FIG. 5, bottom panel, shows cell growth kinetics of edited cells with the same designs measured in editing cells in the top panel. In contrast to editing cells, the growth kinetics of edited cells are comparable regardless of the design, demonstrating that growth kinetics are not a result of fitness effects caused by the genomic edit. Therefore, differential editing kinetics are inherently linked to editing cassette properties and, therefore, can be predicted according to methods and systems disclosed herein, in addition to predicting amplified DNA cassette concentrations. FIG. 6 shows the correlation between predicted design representation and measured design representation using a model trained on features describing editing cassettes and the editing cassette library composition.

According to methods and systems disclosed below, the editing cassette replication strategy, the library splitting strategy, or a combination of both strategies, may be employed to provide a resulting manufactured design cassette concentration such that upon transformation into a cell population, the concentration of edited cells with that edited design is similar to other designs from the library in the cell population.

Figure 7:
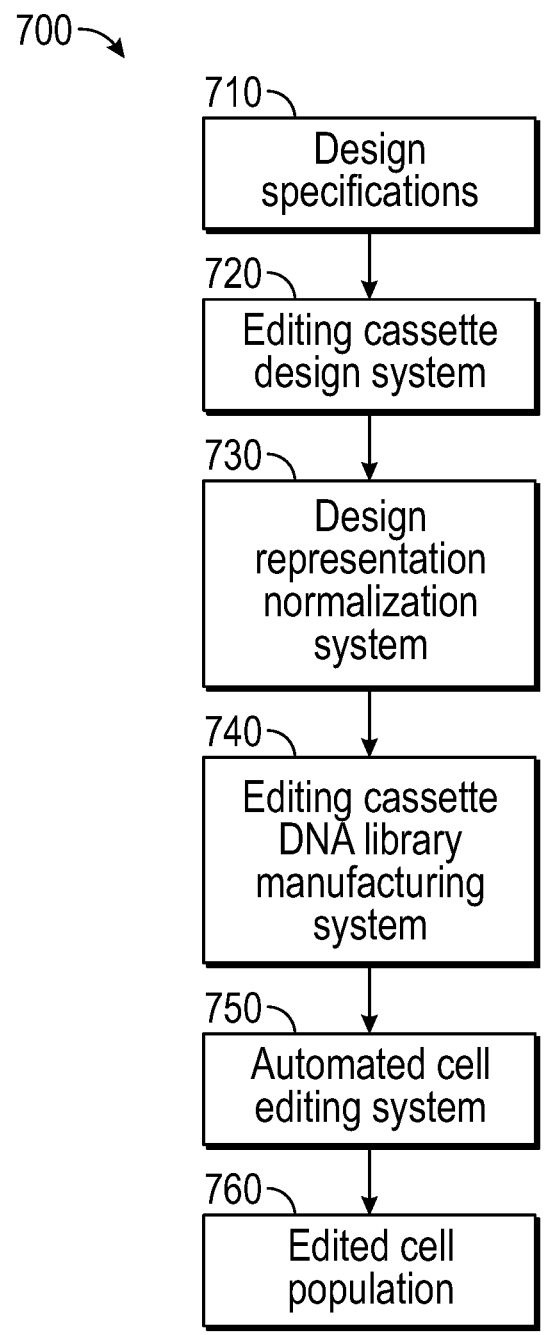
FIG. 7 depicts a system for predicting design representation in a gene-edited cell population according to embodiments.

FIG. 7 depicts a system 700 for predicting design concentrations in a massively parallel-edited cell population, according to disclosed embodiments. Genome editing design specifications 710 are provided by a customer based on customer needs that include designs of oligos to be included in the edited cell population, as well as numbers and/or concentrations of oligos to be included in the edited cell population. In some embodiments, design specifications 710 may include target concentrations, or representations, for each design in a manufactured genetically-edited cell pool. The design specifications 710 are provided to an editing cassette design system 720. In some embodiments, the editing cassette design system 720 may comprise a system that incorporates methods disclosed in pending U.S. patent application Ser. No. 16/903,324 filed on Jun. 16, 2020, entitled, "SYSTEM AND METHOD FOR GENE EDITING CASSETTE DESIGN," assigned to Inscripta, Inc., which is hereby incorporated by reference in its entirety, to produce a library of editing cassette designs.

The cassette designs are provided to a design representation normalization system 730 that will provide predictions of concentrations of the designs in the library within an edited cell population, and develop a strategy to manufacture the designs so that the resulting edited cell population will conform more closely to the design specifications 710, discussed in greater detail below, and in connection with FIGS. 9 and 10. In some embodiments, the design representation normalization system 730 converts editing cassette designs of the library to feature vectors, which may also be referred to herein as sequence embeddings. The designs are provided to one or more NLP systems for conversion to feature vectors. According to certain embodiments, NLP systems that may be employed include and are not limited to machine learning models, and trained machine learning models, such as Word2Vec, Doc2Vec, GloVe, or RandSent, or other NLP machine learning model capable of generating feature vectors from words (e.g., character strings), sentences (e.g., groups of words), paragraphs (e.g., groups of sentences), or documents (e.g., groups of paragraphs). Example features that may be represented in one or more feature vectors are discussed by way of example in connection with FIG. 8, below. The feature vectors are provided to a trained machine learning (ML) model, which could be a "classical" machine learning model, like multivariate linear regression, support vector machine, or gradient boosting regressor, k-means clustering system, a neural network, or an NLP-type neural network model (e.g. an individual skilled in the art of natural language processing will be familiar with architectures like 1D convolutional neural networks, the transformer (attention only), and recurrent neural networks (RNN), such as gated recurrent unit (GRU), long short term memory (LSTM), mLSTM) to determine linguistic distances (or other variances) between each feature vector (e.g., sequence embeddings). Regardless of the model type employed, the output is a prediction of the concentration of each design in a manufactured DNA library or edited cell population, depending on the training task, based on the features represented in the feature vectors generated from the editing cassette designs.

By way of example, for each editing cassette design one or more edit types is predicted, such as a deletion, an insertion, a swap, and a combination swap:insertion. As one or more of these edit types is known to bias edited cell populations, by adjusting the relative concentration of edit cassette designs for manufacturing, the relative concentrations of cell types in a final manufactured edited cell population may be adjusted to conform with the design specifications 710. By way of further example, GC content may be predicted by the machine learning model when provided with the feature vectors. By adjusting editing cassette design concentrations based on GC content, a final manufactured edited cell population may be adjusted to conform to the design specifications 710.

Based on these predictions, a design cassette library may be modified in silico using one or more of the aforementioned modification strategies (e.g., design replication and/or library splitting). According to certain embodiments, parameters used to determine the modification strategy, or combination of modification strategies include the number of and type of oligos in the edited cell population, total number of oligos present in the edited cell population. The modified version(s) of the editing cassette design library may be provided to the previously described trained machine learning model(s) to provide a modified predicted design concentration. If the modified predicted concentration is sufficiently close to the design specification 710, the modified library may then be provided to an editing cassette DNA library manufacturing system 740, for amplification and reagent bundling, producing a set of cell editing cassettes that can be input into an automated cell editing system 750 that produces an edited cell population 760.

Figure 8:
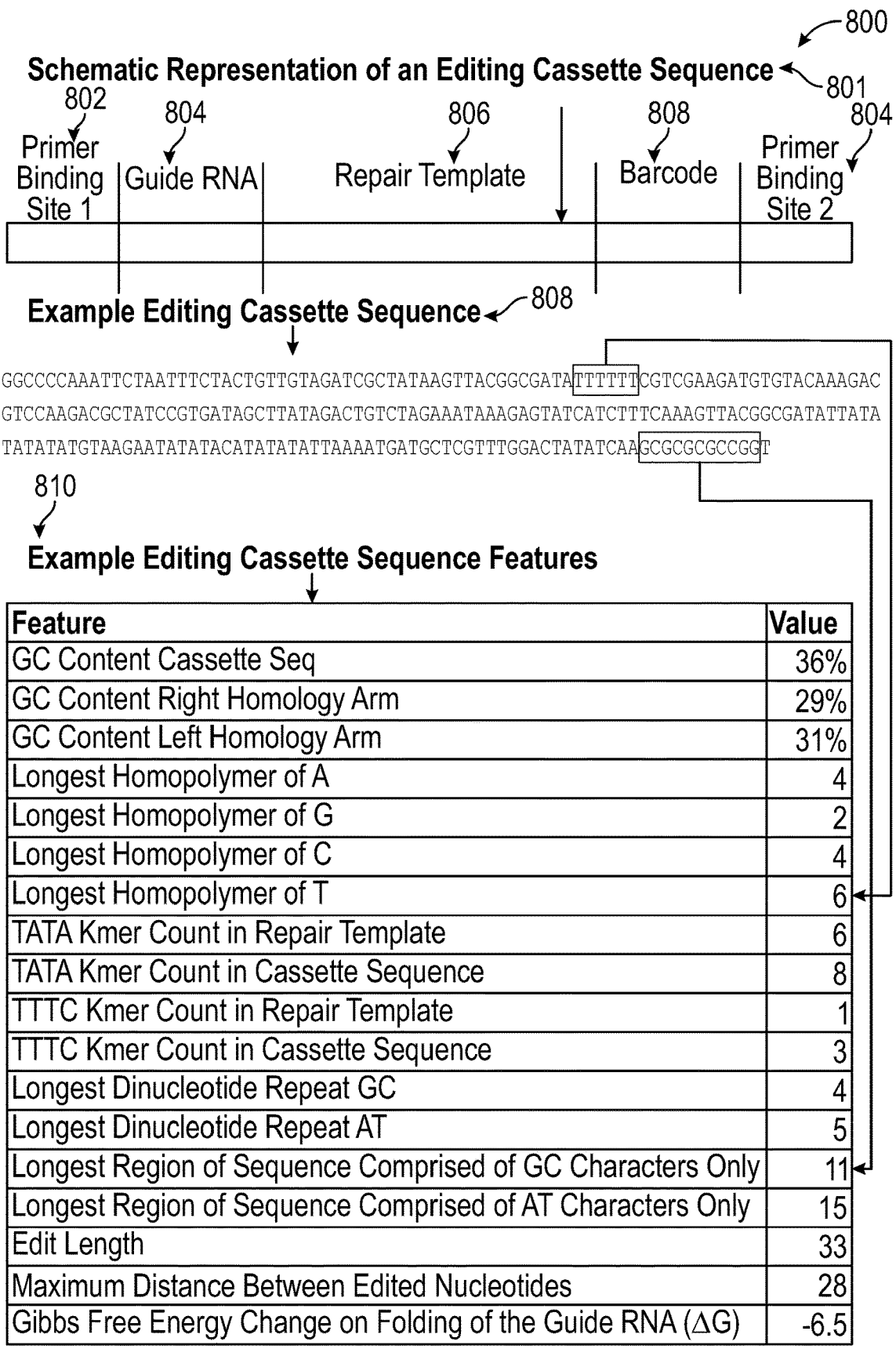
FIG. 8 depicts an example schematic representation of an editing cassette sequence, according to embodiments.

FIG. 8 depicts an example edit cassette design representation 800 of an editing cassette sequence produced by the editing cassette design system 720 of FIG. 7, according to embodiments.

Schematic representation of an example editing cassette sequence 801, such as produced by the editing cassette design system 720 of FIG. 7, depicts the order in which sequence components of an edit cassette design may be configured. Primer binding site 1 802, adjacent guide RNA 804, and primer binding site 2 804, adjacent barcode 808, are the sequences to which amplification primers bind such that the editing cassette may be amplified. Guide RNA 804 depicts the portion of an example editing cassette design that will guide a synthesized version of the editing cassette to the appropriate location on a target sequence to be edited. Repair template 806, sometimes referred to as a homology arm, may comprise a variety of sequences for applying a desired edit to the target sequence such as a user-specified edit, one or more edits targeting the protospacer adjacent motif (PAM) sequence and related edits to prevent further cutting, and intervening ancillary edits. Barcode 808, in embodiments, may identify the target sequence to be edited and include additional information about the sequence such as the editing cassette that was utilized to make the edit.

Example editing cassette sequence 801 depicts an example editing cassette sequence comprised of sequences of base pairs, developed in accordance with design specifications, such as design specifications 710 of FIG. 7.

Example editing cassette sequence features 810 depict example features of example editing cassette sequence 801. The list of example features depicted, such as GC content, homopolymer length, kmer count, dinucleotide repeat, region sequence length, edit length, nucleotide edit distance length, and Gibbs free energy charge, are examples of features that may be used in accordance with the disclosed embodiments. Editing cassette features may be used in connection with determining cassette sequence representation and/or for the determination of library level features that may be predictive of cassette sequence representation in the context of the library of which the cassette sequence is a member.

In some embodiments, a sequence alignment between the target sequence to be edited and the repair template (e.g. the sequence containing edits) is made. This sequence alignment allows calculation of features that are correlated with the kinetics of the editing event that may be used for predicting concentrations of manufactured cassette design or edited cell populations according to embodiments disclosed herein. These features include and are not limited to: the difference between GC content of the reference and the repair template, the length of the edit sequence, the distance between the nuclease cut site and the edit positions (not shown), and the length of repair template sequence upstream and downstream of the edit window that is identical to the reference sequence.

Figure 9:
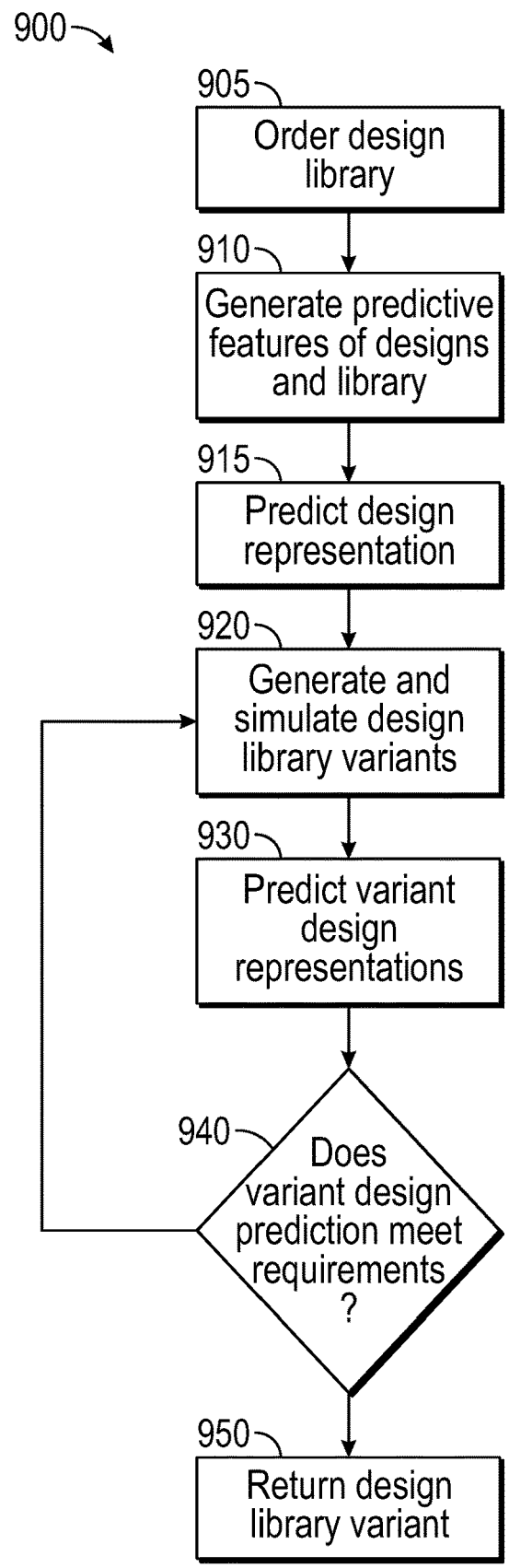
FIG. 9 depicts a flow diagram for predicting design representation and adjusting a design library, according to disclosed embodiments.

FIG. 9 depicts a flow diagram for predicting design representations for a design cassette library, and adjusting the library, according to disclosed embodiments.

At block 905, a design library is ordered by a customer based on the customer's design specifications or edits for editing a population of cells, where the design specification may include a target design representation in a manufactured population of editing cassettes, or a population of edited cells. In embodiments, the customer's design specifications are provided to a gene-editing cassette design system, which in some embodiments may be an automated cassette design system such as the editing cassette design system 720 of FIG. 7. During cassette design, each design will have a number of features associated with it, such as for example, biophysical characteristics, target sequence, homology arm replacement sequence, edit spacing, PAM sequence (e.g., location, type), protospacer sequences (e.g., location, type), chromosomal coordinates of an edit, etc. At block 910, a number of features for each design may be determined, such as example editing cassette sequence features 810 of FIG. 8, that may be predictive of the representation of a design in a manufactured editing cassette population when the designs are synthesized, or in a cell population edited by the synthesized editing cassettes. Features predictive of design representation may include the cut activity score, the length of the edit sequence, GC content, and kmer counts, likelihood that a guide RNA is a fast cutter, the length of sequence identity upstream and downstream of the edit window. Additionally, predictive features are designated for the library of designs, predictive of design representation of a given design relative to other designs of the library. Predictive features for a library may include the data compression ratio, sum or mean or median of distances among cassette features (e.g. GC content and kmer counts), sequence embeddings produced from a neural network, or other features that are predictive of a given cassette design in a given library of designs.

Each editing cassette design is processed by the design representation normalization system 730, forming a feature vector, or sequence embedding, for each design. According to certain embodiments, feature vectors may further include library level features. The features, such as those describe elsewhere herein, are represented in the feature vector form of each editing cassette design. The feature vectors are then classified with a machine learning model described above, based on represented features. Once the editing cassette designs are classified based on their respective feature vectors, predictions are developed for possible edited cell population compositions. Edited cell population compositions are predicted using one or more trained machine learning models, such as multivariate linear regression, support vector machine, gradient boosting regressor, ensemble modeling techniques, or neural network architectures like the transformer architecture (e.g. use of "self-attention"), 1D convolutional neural networks or recurrent neural networks built with architecture like GRU, LSTM, mLSTM.

At block 915, design representations and edited cell population compositions for the library are predicted based on the classified feature vectors using one or more trained supervised machine learning models. As will be discussed in greater detail below with FIG. 10, feature vectors (e.g., sequence embeddings) (which may be considered predictive features) of the designs and of the library are generated from a trained natural language processing (NLP) model, such as word2vec, doc2vec, GloVe, and RandSet, a modified version of one of these, or other NLP model suitable for generating sequence embeddings from designs, and in some embodiments design libraries. The sequence embeddings is used in conjunction with cassette-specific features (e.g., GC content, kmer counts, data compression ratio, likelihood that a guide RNA is a fast cutter, length of the edit window) and library-level features like statistical distance summaries (e.g., sum, mean median of distances among cassette features such as GC content and kmer counts, data compression ratio, likelihood that a guide RNA is a fast cutter, length of the edit window) and linguistic distance metrics of the sequence embeddings (e.g., Hamming distance, Levenshtein distance, and/or other algorithms to determine a sequence edit distance, difference, or other pairwise alignment, between feature vectors) are provided to a machine learning model to predict the representation of each design in a manufactured cell population. One of skill in the art of statistical modeling will understand that models can include decision trees, such as gradient boosting regressor or random forest, support vector machines, neural networks, multivariate linear regression, ensemble models, or a combination of two or more of these.

At block 920, based on the predicted design representation of 915 above, the multiple variants of the design library are developed so as to mitigate predicted over/under representations of a particular design in a manufactured editing cassette and/or edited cell population. Variants are chosen algorithmically using tools including and not limited to Gaussian mixture models, k-means clustering, or integer programming. Variations may include but are not limited to, replicating designs in the library that are predicted to be under-represented in the manufactured cell population, removing designs from the library that are predicted to be over-represented, and splitting the library into groupings of designs that are predicted to be represented substantially equally in the grouping, or a combination of two or more of these, or in the manner indicated by the customer in the design specification.

At block 930, the models are applied to predict design representation for each of the library variants. At block 940, the predictions are compared to the target customer design representation in terms of manufactured editing cassette or edited cell population concentrations. If one (or more) of the variant libraries meets customer requirements, the variant design library/ies is returned at block 950, whereas if no library variants meet customer requirements, additional library variants are developed. A returned library variant that meets customer requirements may be provided directly to a system to synthesize the library, while in other embodiments, a notification may be provided (e.g., visual and/or audio notification via a computing device), and a file is provided containing the library variant.

Figure 10:
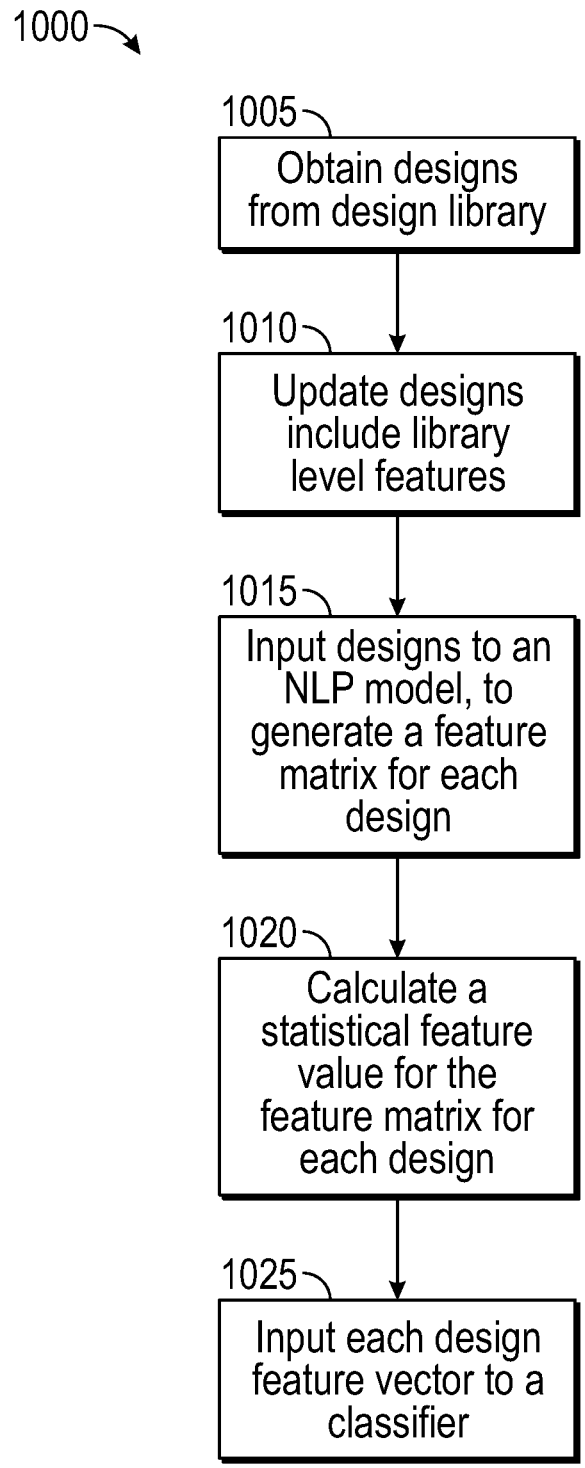
FIG. 10 depicts a flow diagram for predicting design representation, according to embodiments.

FIG. 10 depicts a flow diagram for predicting design representation, according to disclosed embodiments.

Figure 11:
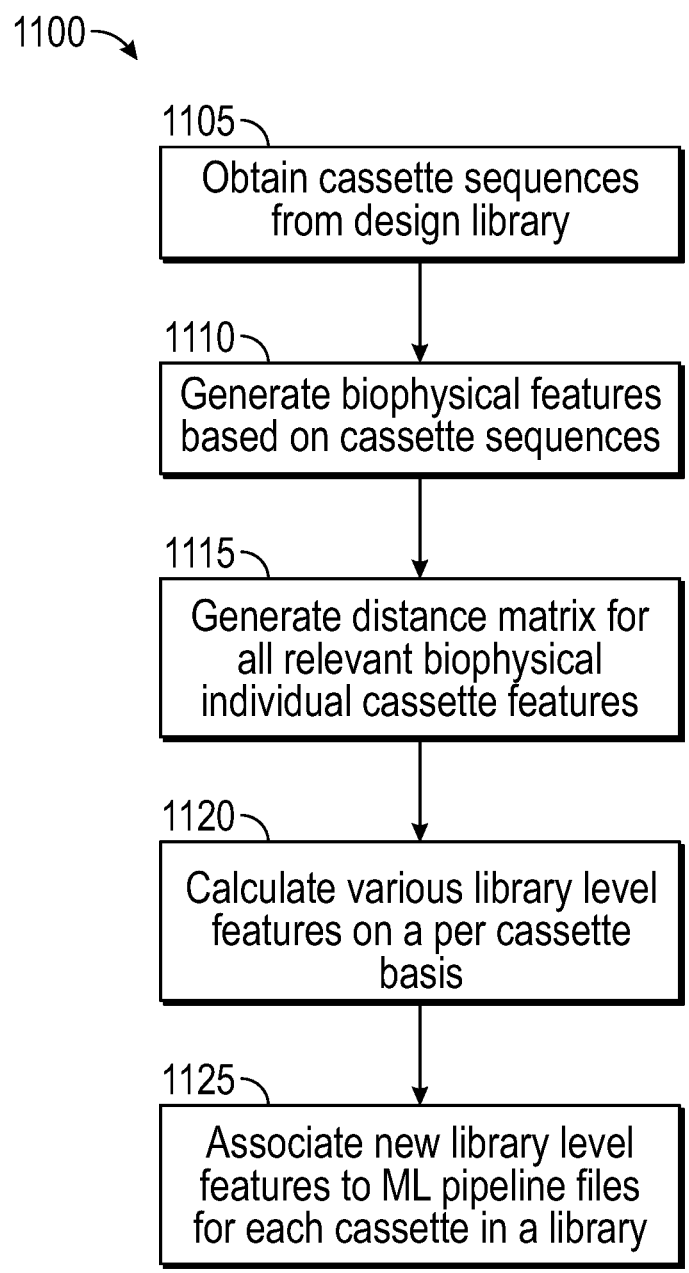
FIG. 11 depicts a process for developing library level features, according to disclosed embodiments.

At block 1005, an input design library is received from a cassette design system, comprising a plurality of editing cassette designs, and individual designs are obtained from the design library. Each design in the design library comprises a number of features related to the design, such as one or more target homology arms, edit type (e.g., swap, replacement, deletion, insertion), edit spacing, edit sequence composition, auxiliary edits, mutated target homology arms, differences in auxiliary edit (e.g., position and number), ancillary edit type, ancillary edit sequence, GC content, data compression ratio, likelihood that a guide RNA is a fast cutter, length of the edit window, the distance between the nuclease cut site and the edit sequence, biophysical features of the design, represented as a design string, such as shown in FIG. 11. At block 1010, each design string is updated to include library features characterizing the design in the context of the library. It should be noted that in some embodiments, designs are not updated to include library features. Library features may include, for example the data compression ratio, sum or mean or median of distances among cassette features (e.g. GC content & kmer counts), sequence embeddings produced from a neural network. An example of the development and implementation of a library level features is discussed further in connection with FIG. 5.

At block 1015, the editing cassette DNA sequences are provided to an NLP machine-learning (ML) model, such as Word2vec, Doc2vec, GloVe, RandSet, or other machine learning model capable of developing relationships between elements of kmers within a design, designs as between each other such as when the designs are part of a library or designs of multiple libraries between each other where the libraries share one or more relationships, to develop sequence embeddings (e.g., feature vectors) as described above in connection with FIG. 9 and below. Disclosed ML models typically utilize a neural network architecture, such as a recurrent neural network or feed-forward neural network, and in embodiments, feedback neural networks may be utilized.

In embodiments, each design is divided into 4 to 7 sequence kmer words for the NLP model. A group of kmers makes up a design, which analogizes to a sentence for the chosen NLP model, and a group of designs makes up a library or pool, analogizing to a document in an NLP model. In embodiments requiring only feature-vector relationships between kmers of a design, a word-embedding model such as Word2vec may be used, whereas, in embodiments in which developing feature-vector relationships between designs in a library are of interest, a model such as Doc2vec may be used.

The NLP model will provide as output a sequence embedding, that is coupled with a feature-matrix for each design.

At block 1020, statistical feature values may be provided for the feature vector matrix of each design, to provide statistical weighting to features that will make the classification step more accurate.

At block 1025, the feature vector matrices are provided to a classifier that will develop groupings, or clusters of designs, based on their respective feature vector matrices. Models may include trained versions of one or more of multivariate linear regression, support vector machine, gradient boosting regressor, ensemble modeling techniques, or neural network architectures like the transformer architecture (e.g. use of "self-attention"), 1D convolutional neural networks or recurrent neural networks built with architecture like GRU, LSTM, mLSTM. Trained models predict each cassette design's relative representation in the manufactured cassette pool or the edited cell population.

FIG. 11 depicts a process 1100 for developing library level features, according to disclosed embodiments. Although GC Content is used in the example below, other features disclosed herein may be similarly developed, in place or, or in addition to GC Content, such as cut activity score, the length of the edit sequence, kmer counts, sequence similarity, data compression ratio, and length of the edit window.

Figure 14:
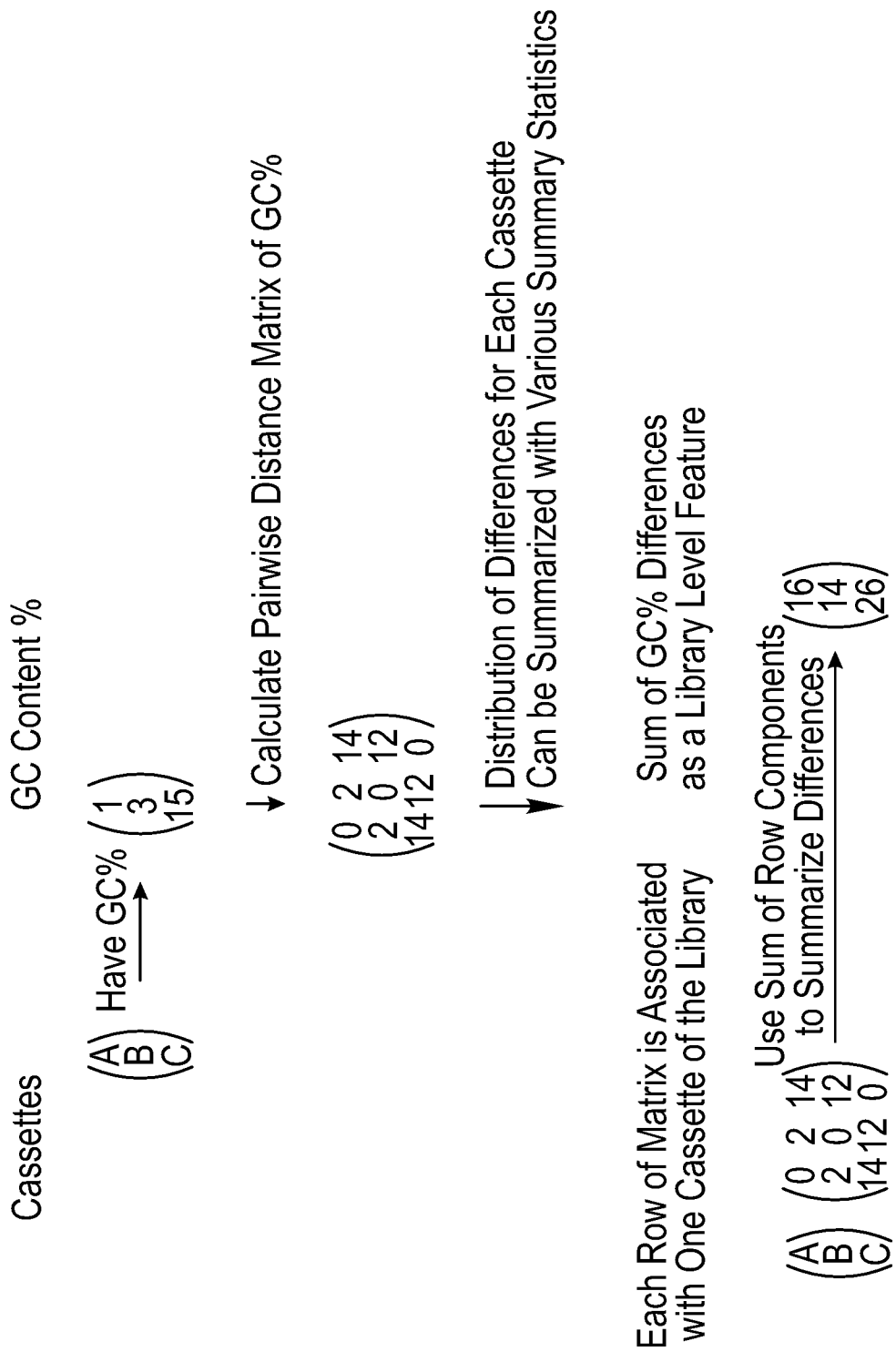
FIG. 14 depicts an exemplary generation of a distance matrix for a numerical feature, according to disclosed embodiments.

At block 1105, the process 1100 obtains cassette sequences, or full designs, from a design library. Numerical features are identified based on each of the cassette sequences at block 1110, such example editing cassette sequence features 810 of FIG. 8 and elsewhere herein. For a relevant numerical feature identified at block 1115, a distance matrix is generated that includes cassette sequences having the numerical feature. An example of generation of a distance matrix for a numerical feature, for example GC content, is shown in FIG. 14 for reference.

At block 1120, using methods disclosed herein, various library level features are developed, on a per cassette basis, and at block 1125, the distance matrices developed for each biophysical feature is associated with each design of the library.

Figure 12:
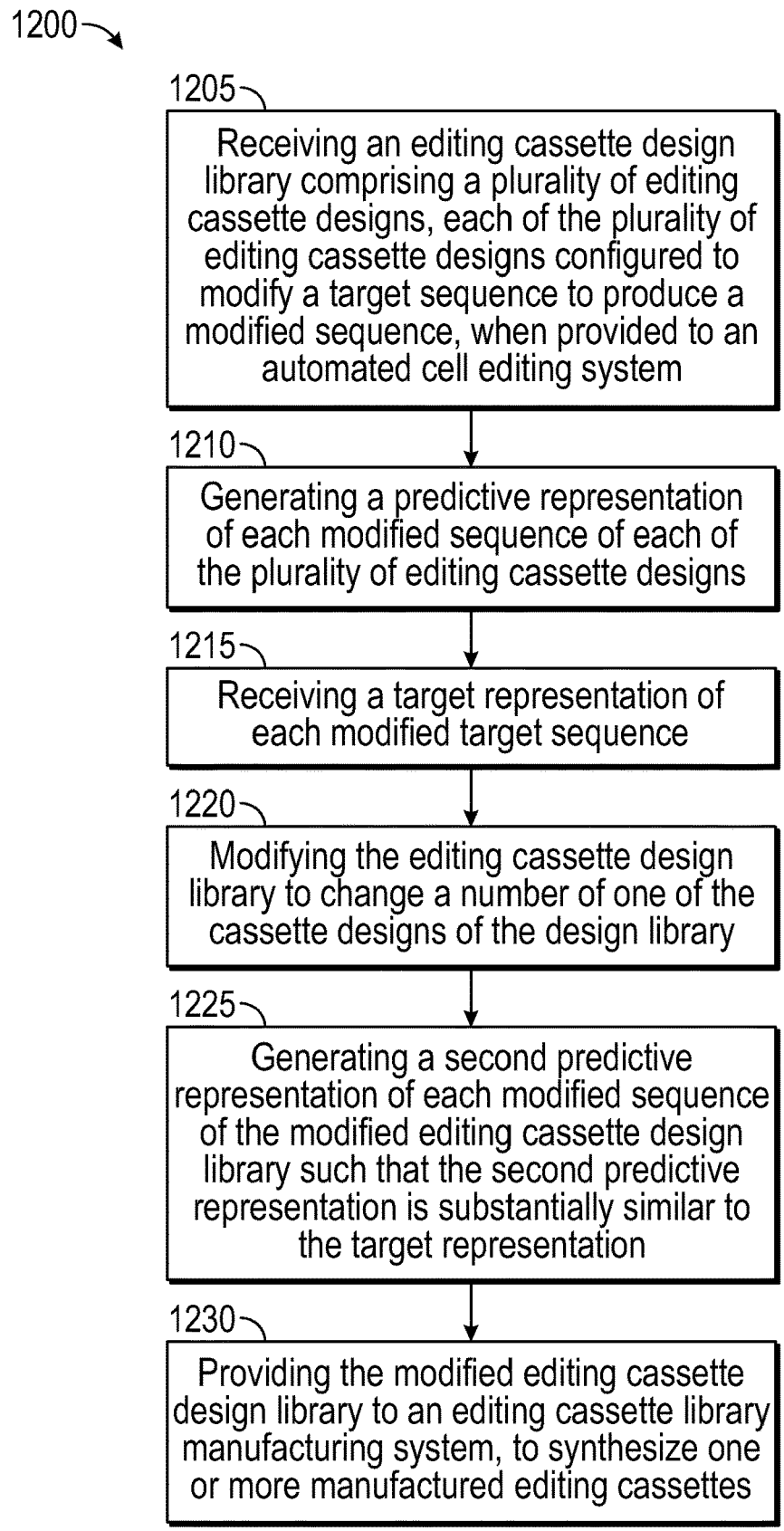
FIG. 12 depicts a method for predictive modeling design representations of a gene-editing cassette design library, according to disclosed embodiments.

FIG. 12 depicts a method 1200 for predictive modeling of a gene-editing cassette design library, according to disclosed embodiments.

At block 1205, an editing cassette design library is received by design representation normalization system 730, comprising a plurality of editing cassette designs, each of the plurality of editing cassette designs configured to modify a target sequence to produce a modified sequence, when provided to an automated cell editing system.

At block 1210, a predictive representation of each modified sequence of each of the plurality of editing cassette designs is generated by design representation normalization system 730.

At block 1215 a target representation of each modified target sequence is received by the design representation normalization system.

At block 1220, the editing cassette design library is modified by the design representation normalization system 730 to change a number of one of the cassette designs of the design library.

At block 1225, a second predictive representation of each modified sequence of the modified editing cassette design library is generated, such that the second predictive representation is substantially similar to the target representation.

Figure 13:
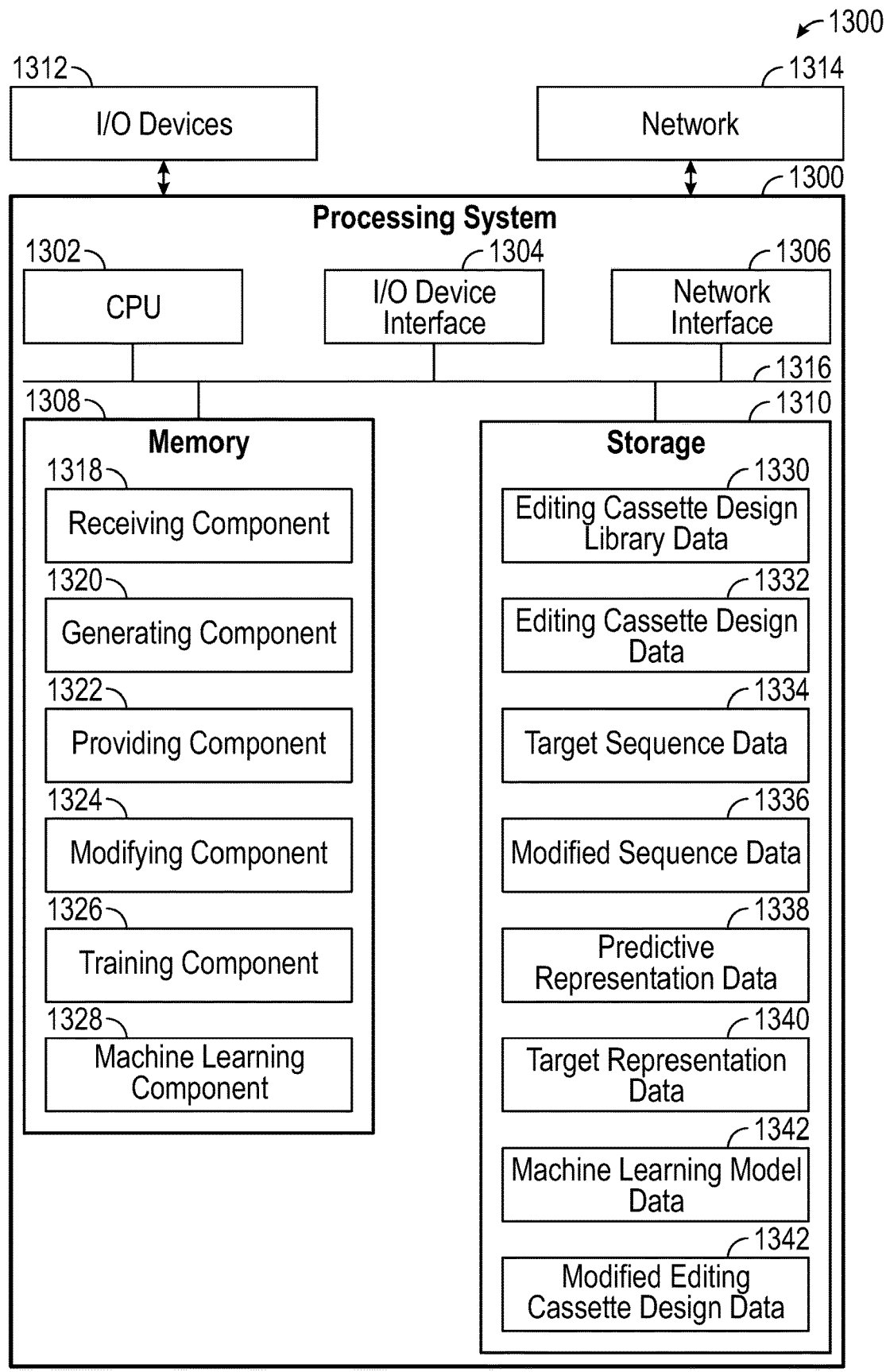
FIG. 13 depicts a processing system for predictive modeling of design representations of a gene-editing cassette design library, according to disclosed embodiments.

At block 1230, the modified editing cassette design library is provided to editing cassette library manufacturing system 740, to synthesize one or more manufactured editing cassettes FIG. 13 depicts a processing system 1300 for predictive modeling of a gene-editing cassette design library that may be used with disclosed embodiments, such as the systems and methods depicted in FIG. 7-12.

Processing system 1300 includes a central processing unit (CPU) 1302 connected to a data bus 1316. CPU 1302 is configured to process computer-executable instructions, e.g., stored in a memory 1308 or a storage 1310, and to cause the processing system 1300 to perform methods described herein, for example with respect to FIGS. 7-12. CPU 1302 is included to be representative of a single CPU, multiple CPUs, a single CPU having multiple processing cores, and other forms of processing architecture capable of executing computer-executable instructions. Although processing system 1300 is depicted as a single physical system, it may be implemented as more than one physical or virtual systems comprising one or more component shown.

Processing system 1300 further includes input/output (I/O) device(s) 1312 and interfaces 1304, which allows processing system 1300 to interface with input/output devices 1312, such as, for example, keyboards, displays, mouse devices, pen input, and other devices that allow for interaction with processing system 1300. Note that processing system 1300 may connect with external I/O devices through physical and wireless connections.

Processing system 1300 further includes a network interface 1306, which provides processing system 1300 with access to external network 1314 and thereby external computing devices.

Processing system 1300 further includes memory 1308, which in this example includes a receiving component 1318, generating component 1320, providing component 1322, modifying component 1324, training component 1326, and a machine learning component 1328 for performing operations described in FIGS. 7-12.

Note that while shown as a single memory 1308 in FIG. 13 for simplicity, the various aspects stored in memory 1308 may be stored in different physical memories, including memories remote from processing system 1300, but all accessible by CPU 1302 via internal data connections such as bus 1316.

Storage 1310 further includes editing cassette design library data 1330, which may be like the design library described in connection with FIGS. 1, 2, and 7-12, and editing cassette design data 1332, which may be like the cassette design(s) described in connection with FIGS. 1, 2, and 7-12. Storage 1310 further includes target sequence data 1334 and modified sequence data 1336, which may be like the target sequence and modified sequence described in connection with the FIGS. 1, 2, and 7-12. Further included are predictive representation data 1338 and target representation data 1340, described in connection with the FIGS. 1, 2, and 7-12, and machine learning model data 1342, described in connection with machine learning models in FIGS. 1, 2, and 7-12, and modified editing cassette design data, described in connection with FIGS. 1, 2, and 7-12.

While not depicted in FIG. 13, other aspects may be included in storage 1310.

As with memory 1308, although a single storage 1310 is depicted in FIG. 13 for simplicity; various aspects stored in storage 1310 may be stored in different physical or virtual storages, all accessible to CPU 1302 via internal data connections, such as bus 1316, or external connection, such as network interfaces 1306. One of skill in the art will appreciate that one or more elements of the processing system 1300 may be located remotely and accessed via a network 1314.

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented, or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a c c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory), and the like. Also, "determining" may include resolving, selecting, choosing, establishing, and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to, a circuit, an application-specific integrated circuit (ASIC), or processor. Generally, where there are operations illustrated in FIG.s, those operations may have corresponding counterpart means-plus-function components with similar numbering.

The various illustrative logical blocks, modules and circuits described in connection with the present disclosure may be implemented or performed with a general-purpose processor, a digital signal processor (DSP), an application-specific integrated circuit (ASIC), a field-programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

A processing system may be implemented with a bus architecture. The bus may include any number of interconnecting buses and bridges depending on the specific application of the processing system and the overall design constraints. The bus may link together various circuits including a processor, machine-readable media, and input/output devices, among others. A user interface (e.g., keypad, display, mouse, joystick, etc.) may also be connected to the bus. The bus may also link various other circuits such as timing sources, peripherals, voltage regulators, power management circuits, and other circuit elements that are well known in the art, and therefore, will not be described any further. The processor may be implemented with one or more general-purpose and/or special-purpose processors. Examples include microprocessors, microcontrollers, DSP processors, and other circuitry that can execute software. Those skilled in the art will recognize how best to implement the described functionality for the processing system depending on the particular application and the overall design constraints imposed on the overall system.

If implemented in software, the functions may be stored or transmitted over as one or more instructions or code on a computer-readable medium. Software shall be construed broadly to mean instructions, data, or any combination thereof, whether referred to as software, firmware, middleware, microcode, hardware description language, or otherwise. Computer-readable media include both computer storage media and communication media, such as any medium that facilitates the transfer of a computer program from one place to another. The processor may be responsible for managing the bus and general processing, including the execution of software modules stored on the computer-readable storage media. A computer-readable storage medium may be coupled to a processor such that the processor can read information from, and write information to, the storage medium. In the alternative, the storage medium may be integral to the processor. By way of example, the computer-readable media may include a transmission line, a carrier wave modulated by data, and/or a computer-readable storage medium with instructions stored thereon separate from the wireless node, all of which may be accessed by the processor through the bus interface. Alternatively, or in addition, the computer-readable media, or any portion thereof, may be integrated into the processor, such as the case may be with cache and/or general register files. Examples of machine-readable storage media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may be embodied in a computer-program product.

A software module may comprise a single instruction, or many instructions, and may be distributed over several different code segments, among different programs, and across multiple storage media. The computer-readable media may comprise a number of software modules. The software modules include instructions that, when executed by an apparatus such as a processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During the execution of the software module, the processor may load some of the instructions into a cache to increase access speed. One or more cache lines may then be loaded into a general register file for execution by the processor. When referring to the functionality of a software module, it will be understood that such functionality is implemented by the processor when executing instructions from that software module.

While the foregoing is directed to embodiments of the present disclosure, other and further embodiments of the disclosure may be devised without departing from the basic scope thereof, and the scope thereof is determined by the claims that follow.

What is claimed is:

1. A method for modifying an editing cassette design library composition, comprising:
   receiving an editing cassette design library comprising a plurality of editing cassette designs, each of the plurality of editing cassette designs configured to modify a target sequence to produce a modified sequence when provided to an automated cell editing system;
   generating one or more feature vectors associated with each of the plurality of editing cassette designs, the feature vectors comprising cassette features predictive of a representation for each of the plurality of editing cassette designs upon editing with the editing cassette design library;

generating a predictive representation of each modified sequence of each of the plurality of editing cassette designs using one or more trained machine learning (ML) models, the one or more trained ML models trained to generate the predictive representation based on the one or more feature vectors associated with each of the plurality of editing cassette designs;

receiving a target representation of each modified target sequence;

modifying the editing cassette design library to change one or more editing cassette designs of the editing cassette design library;

generating a second predictive representation of each modified sequence of the modified editing cassette design library using the one or more trained machine learning models; and providing the modified editing cassette design library based on the second predictive representation and the target representation.

2. The method of claim 1, wherein modifying the editing cassette design library comprises removing at least one of the editing cassette designs from the editing cassette design library.

3. The method of claim 2, wherein modifying the editing cassette design library comprises placing at least one of the editing cassette designs in a second editing cassette design library.

4. The method of claim 1, wherein modifying the editing cassette design library comprises updating the editing cassette design library to include an additional instance of at least one of editing cassette designs.

5. The method of claim 1 wherein generating the predictive representation comprises:
classifying each feature vector based on features of each respective feature vector using a trained first machine learning (ML) model; and
predicting relative representation of the plurality of editing cassette designs using regression, based on the classifying, using a trained second ML model.

6. The method of claim 5, wherein the cassette features comprise at least one of an edit type, an edit length, a sequence composition, an auxiliary edit position, an auxiliary edit number, manufacturing complexity of the editing cassette design library, edit type complexity of the editing cassette design library, and edit length complexity of the editing cassette design library.

7. The method of claim 6, wherein the generating the one or more feature vectors comprises encoding each of the editing cassette designs with one of Word2vec, Doc2vec, GloVe, or RandSent.

8. The method of claim 7, wherein the first ML model comprises one or more of a multivariate linear regressor, a support vector machine, a gradient boosting regressor, ensemble model, or a neural network.

9. A system comprising:
one or more memory devices;
a processor configured to execute computer-readable instructions comprising a method for adjusting a genome design library composition, that causes the processor to:
receive an editing cassette design library comprising a plurality of editing cassette designs, each of the cassette designs configured to modify a target sequence to produce a modified sequence when provided to an automated cell editing system;
generate one or more feature vectors associated with each of the plurality of editing cassette designs, the feature vectors comprising cassette features predictive of a representation for each of the plurality of editing cassette designs upon editing with the editing cassette design library;
generate a predictive representation of each modified sequence of each of the plurality of editing cassette designs using one or more trained machine learning (ML) models, the one or more trained ML models trained to generate the predictive representation based on the one or more feature vectors associated with each of the plurality of editing cassette designs;
receive a target representation of each modified target sequence;
modify the editing cassette design library to change one or more cassette designs of the design library;
generate a second predictive representation of each modified sequence of the modified editing cassette design library using the one or more trained machine learning models; and
provide the modified editing cassette design library based on the second predictive representation and the target representation.

10. The system of claim 9, wherein the computer-readable instructions that cause the processor to modify the editing cassette design library comprises removing at least one of the editing cassette designs from the editing cassette design library.

11. The system of claim 10, wherein the computer-readable instructions that cause the processor to modify the editing cassette design library comprises placing at least one of the editing cassette designs in a second editing cassette design library.

12. The system of claim 9, wherein the computer-readable instructions that cause the processor to modify the editing cassette design library comprises updating the editing cassette design library to include an additional instance of at least one of the editing cassette designs.

13. The system of claim 9, wherein the computer-readable instructions that cause the processor to generate the predictive representation further causes the processor to:
classify each feature vector based on features of each respective feature vector, using a trained first machine learning (ML) model; and
predict a relative representation of the plurality of editing cassette designs using regression, based on the classifying, using a trained second ML model.

14. The system of claim 13, wherein the cassette features comprise at least one of an edit type, an edit length, a sequence composition, an auxiliary edit position, an auxiliary edit number, manufacturing complexity of the editing cassette design library, edit type complexity of the editing cassette design library, and edit length complexity of the editing cassette design library.

15. The system of claim 14 wherein the computer-readable instructions that cause the processor to generate the one or more feature vectors comprises encoding each of the editing cassette designs with on of word2vec, doc2vec, GloVe, and RandSent.

16. The system of claim 14, wherein the first ML model comprises one or more of a multivariate linear regressor, a support vector machine, a gradient boosting regressor, ensemble model, or a neural network.

17. A non-transitory computer-readable medium comprising computer-readable instructions for a method for adjusting a genome design library composition, the computer readable instructions configured to cause a processor to:
- receive an editing cassette design library comprising a plurality of editing cassette designs, each of the cassette designs configured to modify a target sequence to produce a modified sequence when provided to an automated cell editing system;
- generate one or more feature vectors associated with each of the plurality of editing cassette designs, the feature vectors comprising cassette features predictive of a representation for each of the plurality of editing cassette designs upon editing with the editing cassette design library;
- generate a predictive representation of each modified sequence of each of the plurality of editing cassette designs using one or more trained machine learning (ML) models, the one or more trained ML models trained to generate the predictive representation based on the one or more feature vectors associated with each of the plurality of editing cassette designs;
- receive a target representation of each modified target sequence;
- modify the editing cassette design library to change one or more cassette designs of the design library;
- generate a second predictive representation of each modified sequence of the modified editing cassette design library such that the second predictive representation is substantially similar to the target representation; and
- providing the modified editing cassette design library based on the second predictive representation and the target representation.

18. The non-transitory computer-readable medium of claim 17, wherein the computer-readable instructions that cause the processor to modify the editing cassette design library comprises one of:
- removing at least one of the editing cassette designs from the editing cassette design library;
- placing the at least one of the editing cassette designs in a second editing cassette design library; or
- updating the editing cassette design library to include an additional instance of at least one of the editing cassette designs.

19. The non-transitory computer-readable medium of claim 17, wherein the computer-readable instructions that cause the processor to generate the predictive representation further causes the processor to:
- classify each feature vector based on features of each respective feature vector, using a trained first machine learning (ML) model; and
- predict a relative representation of the plurality of editing cassette designs using regression, based on the classifying, using a trained second ML model.

20. The non-transitory computer-readable medium of claim 19, wherein the cassette features comprise at least one of an edit type, an edit length, a sequence composition, an auxiliary edit position, an auxiliary edit number, manufacturing complexity of the editing cassette design library, edit type complexity of the editing cassette design library, and edit length complexity of the editing cassette design library.

* * * * *